United States Patent [19]

Elion et al.

[11] 4,055,514

[45] Oct. 25, 1977

[54] CATALYST FOR PREPARATION OF 4-CYANOTHIAZOLE

[75] Inventors: Glenn R. Elion, Avenel; Arthur E. Klink, Lebanon, both of N.J.

[73] Assignee: Merck & Co., Inc., Rahway, N.J.

[21] Appl. No.: 666,714

[22] Filed: Mar. 15, 1976

[51] Int. Cl.² .............................................. B01J 23/88
[52] U.S. Cl. .................................. 252/470; 260/302 R
[58] Field of Search ...................... 252/470; 260/302 R

[56] References Cited

U.S. PATENT DOCUMENTS 3,843,555  10/1974  Erpenbach et al. ................. 252/470

FOREIGN PATENT DOCUMENTS 988,956  4/1965  United Kingdom ............ 260/302 R

Primary Examiner—W. J. Shine
Attorney, Agent, or Firm—David L. Rose; Richard A. Thompson; Harry E. Westlake

[57] ABSTRACT

4-Cyanothiazole is prepared by the catalytic vapor phase ammoxidation of 4-methylthiazole using a novel catalyst composition comprising a cobalt molybdate catalyst wetted with different levels of potassium hydroxide. The process affords high selectivity to the desired 4-cyanothiazole.

2 Claims, No Drawings

CATALYST FOR PREPARATION OF 4-CYANOTHIAZOLE

This invention relates to novel chemical catalyst compositions and to a process for the production of 4-cyanothiazole from 4-methylthiazole using such compositions as catalysts.

One of the problems inherent in an ammoxidation system for making cyanothiazole from 4-methylthiazole in a system employing excess oxygen in the reactant stream is undesirable combustion of the organic reactant and ammonia to unwanted by-products. This, of course, adds to process costs in that more reactant is required to produce a given amount of cyano compound (e.g., yields are reduced) and also larger capital investment is required to build a plant for a given capacity. Thus, a reduction in the undesired combustion of ammonia and organic reactant with the attendant yield increase is a desirable objective.

It has now been found that in the catalytic vapor phase ammoxidation of 4-methylthiazole to 4-cyanothiazole, the yield of 4-cyanothiazole can be significantly increased, and ammonia and thiazole decomposition mitigated, by utilizing as catalyst the novel catalyst composition described herein. An advantage of the present invention is that the catalyst is more selective for production of the desired 4-cyanothiazole.

Another advantage is that an adiabatic or isothermal-type reactor can be utilized which results in allowance of temperature fluctuations without any significant decrease in the high selectivity for 4-cyanothiazole.

Thus according to the invention, there is provided a process for the preparation of 4-cyanothiazole from 4-methylthiazole which comprises passing as a reactant stream a gaseous mixture comprising
1. 4-methylthiazole;
2. ammonia;
3. oxygen; and
4. water as steam, and the improvement comprises passing said reactant stream over a graded bed cobalt molybdate ammoxidation catalyst that has been treated with various levels of potassium hydroxide at a temperature of 360° C. to 450° C.

The novel ammoxidation catalyst is a potassium hydroxide treated cobalt molybdate having a molybdenum: cobalt molar ratio from 1.20:1.00 to 1.05:1.00 and the potassium:cobalt molar ratio ranges gradiently from 0.001:1.0 to 0.1:1.0. Preferably, the molar ratio of molybdenum:cobalt is 1.15:1.00 and the potassium:cobalt molar ratio from 0.005:1.0 to 0.025:1.0.

More preferably the molar ratios of the reactant stream are:

ammonia:4-methylthiazole, 1:1 to 2:1;
oxygen:4-methylthiazole, 0.5: to 200:1; and
water as steam:4-methylthiazole 0.001:1 to 10:1.

The novel ammoxidation catalyst is prepared by contacting batches of solid cobalt molybdate with various amounts of potassium hydroxide. The batches are dried and then fired for about 4 hours at 450° C. The potassium hydroxide-treated batches of cobalt molybdate are then placed in a reactor to form a graded catalyst bed so that the cobalt molybdate with the least amount of potassium hydroxide is near the entry end of the reactor and the cobalt molybdate treated with the greatest amount of potassium hydroxide is at the exit end of the reactor.

In carrying out the process of the invention, the reactor and attendant equipment is prepared in the usual way, the reactor being charged with catalyst and otherwise prepared for start-up. The 4-methylthiazole, ammonia, oxygen and water as steam are passed over the catalyst at reaction conditions and at certain mole percent ratios. For an isothermal reactor system, the temperature range can be from 360° C. to 430° C. A more desired range for an isothermal reactor system is 395° C. to 405° C. For an adiabatic reactor system, the outlet temperature range is from about 390° C. to 450° C. A more desirable temperature range for an adiabatic reactor system is 420° C. to 440° C.

The contact time for a reactant stream is the time that the reactants are in contact with the catalyst composition. For an isothermal or adiabatic reactor system, the contact time can be from about 0.1 to 1.0 seconds. A more desirable range is 0.25 to 0.35 seconds.

The following examples are given for the purpose of illustration and not for the purpose of limiting the scope of invention.

EXAMPLE 1

This example illustrates the preparation of the potassium hydroxide cobalt molybdate catalyst using the incipient wetness technique. Cobalt molybdate may be prepared by techniques known in the art. That is, cobalt molybdate is precipitated by reacting cobalt sulfate or nitrate with ammonium molybdate. However, the subsequent potassium hydroxide treatment and graded bed technique result in the novel catalyst and ammoxidation process.

1. To 150 ml. of water is added 145.0 gm. of cobalt nitrate and the mixture is heated to 35° C. with stirring until all the material is in solution.

2. To 200 ml. of water is added 89.7 gm. of ammonium paramolybdate and the mixture heated to 35° C. with stirring under essentially all the material is in solution. The solution is then filtered to remove insoluble particulate matter.

The solutions obtained in steps 1. and 2. above are mixed and then 90 ml. of ammonium hydroxide solution (14%) is added with continued agitation at a rate of 3 ml./minute at 35° C.

The resulting cobalt molybdate precipitate is filtered, washed with 200 ml. of water at 30° C. and dried for about 48 hours in a vacuum oven at 15–20 millimeters Hg at 80°–90° C. The catalyst compound is then fired for 18 hours in air at 450° C., screened to remove fines, and sized to 16–30 mesh. The molar ratio of Mo:Co is 1.15:1.00.

To prepare the improved catalyst, five 10-gm. batches of the basic catalyst are treated with potassium hydroxide solutions. Each 10-gm. batch is treated with a different normality solution by the incipient wetness technique. By the term "incipient wetness" is meant that the inner pores of the catalyst are filled with solution without leaving the surface wetted. The catalyst is titrated with one of the potassium hydroxide solutions until the catalyst particles are no longer free flowing, but adhere to each other. At this point, the catalyst pores have filled and the surface is being wetted. Enough dry catalyst is added back to the wetted catalyst until it just becomes free flowing again. At this point, the catalyst is incipient wetted. Each 10-gm. batch is treated respectively with 4.0 ml. of 0.05N KOH solution, 0.10N KOH solution, 0.15N KOH solution, 0.20N KOH solution and vacuum dried at 85° C. for 10 hours, then calcined at 450° C. for 10 hours. The calcined catalysts are placed in a reactor tube in a graded bed so that the batch treated with the least amount of potassium hydroxide is nearest the entry end of the reactor with each higher potassium hydroxide level of treated catalyst following respectively so that the highest potassium hydroxide-treated catalyst is at the outlet end of the reactor tube.

The 0.5N potassium hydroxide-treated catalyst has a potassium:cobalt molar ratio of 0.005:1.0; the 0.10N KOH treated catalyst has a potassium-cobalt molar ratio of 0.01:1.0; the 0.15N KOH-treated catalyst has a potassium:cobalt molar ratio of .015:1.0; the 0.2N KOH-treated catalyst has a potassium:cobalt molar ratio of .02:1.0; and the 0.25N KOH-treated catalyst has a potassium:cobalt molar ratio of .025:1.0.

EXAMPLE 2

In this example, the catalyst bed prepared in Example 1 is utilized.

Ninety (90) cc. of the catalyst in a graded bed are loaded into a 5.08 cm. (2-inch) laboratory adiabatic reactor. The feed composition is adjusted to enter the reactor at 20 cc./hour of 4-methylthiazole, 24 cc./hour of concentrated ammonia ($NH_4OH$ - 28%) and 10 liters/minute of dry air (measured at 20° C.; 1 atmosphere).

At an outlet reactor temperature of 410° C., the conversion is 54% with a selectivity of 66% to 4-cyanothiazole. Comparison with the untreated cobalt molybdate shows this to be a 12% selectivity improvement.

EXAMPLE 3

This example illustrates the cobalt molybdate catalyst where the catalyst has been treated with a single level of potassium hydroxide. The catalyst bed therefore does not contain different levels of potassium hydroxide-treated treated cobalt molybdate. In this example, the catalyst bed is comprised of cobalt molybdate that has been treated with 4.0 ml. of 0.27N potassium hydroxide. The method of catalyst preparation is the same as that utilized in Example 1.

Into a 0.635 cm. stainless steel reactor tube is located 3.6 cc. of the catalyst. The reactor is placed in an isothermal gas chromatographic reactor system. The feed composition is adjusted to enter the reactor at 0.018 cc./minute of 4-methylthiazole, 0.013 cc./minute of concentrated $NH_4OH$ (28%) and 600 cc./minute of dry air. Under the temperature conditions as shown in Table I, the following conversion and selectivity to 4-cyanothiazole is given.

Table I

| Reactor Temp. (° C.) | Conversion (%) | Selectivity (%) |
|---|---|---|
| 430 | 19 | 61 |
| 420 | 15 | 65 |
| 410 | 11 | 71 |

EXAMPLE 4

This example illustrates the use of cobalt molybdate catalyst untreated with potassium hydroxide.

Into a 0.635 cm. stainless steel reactor tube is loaded 3.6 cc. of cobalt molybdate catalyst. The reactor is placed in an isothermal gas chromatographic reactor system. The feed composition is adjusted to enter the reactor at 0.018 cc./minute of 4-methylthiazole, 0.013 cc./minute of concentrated $NH_4OH$ (28%) and 600 cc./minute of dry air. Under the temperature conditions as shown in Table II, the following conversion and selectivity to 4-cyanothiazole is given.

Table II

| Reactor Temp. (° C.) | Conversion (%) | Selectivity (%) |
|---|---|---|
| 420 | 69 | 43 |
| 410 | 54 | 54 |
| 400 | 43 | 57 |
| 390 | 34 | 60 |
| 380 | 23 | 64 |

What is claimed is:

1. An ammoxidation catalyst composition prepared by the process of treating cobalt molybdate with a solution of potassium hydroxide, drying and firing for about 4 hours at 450° C, wherein the molybdenum cobalt molar ratio is from 1.20:1.00 to 1.05:1.00 and potassium cobalt molar ratio from 0.001:1.0 to 0.1:1.0.

2. An ammoxidation catalyst composition according to claim 1 wherein the molybdenum:cobalt molar ratio is 1.15:1.0 and the potassium: cobalt molar ratio is from 0.005:1.0 to 0.025:1.0.

* * * * *